United States Patent [19]

Selinger et al.

[11] Patent Number: 5,840,768
[45] Date of Patent: Nov. 24, 1998

[54] MCC: ALGINATE PHARMACEUTICAL SUSPENSIONS

[75] Inventors: Edward Selinger, Langhorne; Sheila M. Dell, New Hope, both of Pa.; John A. Colliopoulos, Princeton Junction, N.J.; William J. Reilly, Jr., New Hope, Pa.

[73] Assignee: FMC Corporation, Philadelphia, Pa.

[21] Appl. No.: 869,039

[22] Filed: Jun. 4, 1997

[51] Int. Cl.⁶ .......................... A61K 47/00; A61K 31/19; A61K 31/16; A61K 33/08
[52] U.S. Cl. .......................... 514/779; 514/570; 514/629; 514/781; 424/690; 424/693
[58] Field of Search ...................................... 424/690, 693; 514/629, 570, 779, 781

[56] References Cited

U.S. PATENT DOCUMENTS

| | | |
|---|---|---|
| 4,427,681 | 1/1984 | Munshi . |
| 5,366,742 | 11/1994 | Tuason, Jr. et al. . |
| 5,605,712 | 2/1997 | Bertrand et al. .......................... 426/565 |

*Primary Examiner*—Raymond Henley, III
*Attorney, Agent, or Firm*—Paul F. Prestia; Robert L. Andersen

[57] ABSTRACT

Novel pharmaceutical suspensions comprising a pharmaceutically active ingredient suspended in aqueous media with a suspending agent comprising attrited microcrystalline cellulose coprocessed and at least partially surface coated with a calcium sodium alginate salt complex barrier dispersant and readily dispersible and hydratable dry formulations thereof are described and exemplified.

8 Claims, No Drawings

MCC: ALGINATE PHARMACEUTICAL SUSPENSIONS

FIELD OF THE INVENTION

The present invention relates to pharmaceutical suspensions. More particularly it relates to stable pharmaceutical suspensions in which the active ingredient is suspended with attrited microcrystalline cellulose coprocessed and at least partially coated with a calcium/sodium alginate complex as a barrier dispersant. The invention also provides a dry, hydratable, pharmaceutical formulation suitable for reconstitution into such suspensions.

BACKGROUND OF THE INVENTION

Microcrystalline cellulose (MCC) is well known in the pharmaceutical art as an excipient for various solid pharmaceutical dosage forms, for example pharmaceutical tablets. However, it has no practical utility for pharmaceutical suspensions which contain water insoluble or only slightly soluble active ingredients. Colloidal microcrystalline cellulose, also known as attrited microcrystalline cellulose, has been used as a food additive and/or fat replacer for various food products, either alone or coprocessed with other additives such as carboxymethylcellulose. U.S. Pat. No. 4,427,681 also discloses the use of attrited microcrystalline cellulose coprocessed with carboxymethyl cellulose, together with titanium dioxide as an opacifying agent, for thixotropic pharmaceutical gels. The thixotropic formulations are characterized as having a viscosity of from 6000 to 8000 cps prior to being shaken and only 300 to 800 cps after being shaken for five seconds.

Attrited microcrystalline cellulose at least partially coated with a barrier dispersant of an alginate calcium/sodium salt complex is disclosed in U.S. Pat. No. 5,366,742, which is incorporated herein by reference. The MCC:Alginate complex described in the patent is available commercially as a food additive as Avicel® AC-815 from FMC Corporation, Philadelphia, Pa., USA. The patent describes the preparation of such MCC:Alginate complex compositions and their use in various food systems, for example, for milk gelling systems such as milk pudding/pie filing formulations, for suspending cocoa in dry cocoa mixes, for frozen desserts, and for salad dressings.

It has now been found that such MCC:Alginate complex compositions provide excellent suspending agents for water insoluble or slightly soluble pharmaceutical active ingredients, that suspensions made therewith have excellent stability, are redispersible with minimal agitation and/or shearing and tend to maintain their viscosity even under high shear conditions. Moreover, formulation of these MCC:Alginate complexes with such pharmaceutical actives as a dry powder produce an excellent dry readily hydratable and dispersible formulation for reconstitution into such pharmaceutical suspensions.

SUMMARY OF THE INVENTION

The present invention thus embraces two embodiments of the invention. In the first embodiment there is provided an improved pharmaceutical suspension comprising water, a pharmaceutical active and a suspending agent comprising the MCC:Alginate complex. In the second embodiment there is provided a dry readily rehydratable and dispersible powder formulation comprising the pharmaceutical active blended with the MCC:Alginate complex which is readily reconstitutible into the pharmaceutical suspensions of the invention.

DETAILED DESCRIPTION OF THE INVENTION

In the first aspect, the invention comprises an improved pharmaceutical suspension comprising water, a pharmaceutically effective amount of a substantially water insoluble or slightly water soluble active ingredient, and from 0.5% to 10% by weight of the suspension of suspending agent comprising 80% to 90% by weight attrited microcrystalline cellulose at least partially surface coated with 10% to 20% by weight of a calcium/sodium alginate salt complex barrier dispersant, said suspension having a pH of at least 3.5.

The suspending agent used in the invention comprises the MCC:Alginate complex compositions described above, in which the weight ratio of microcrystalline cellulose to alginate salt complex is in the range of 8:1 to 9:1. The preferred embodiment is one in which there is employed about 85% microcrystalline cellulose and about 15% of the alginate complex salt. The alginate salt complex itself advantageously comprises a complex of calcium and sodium salts of alginic acid in which the ratio of calcium to sodium is advantageously in the range of about 0.43:1 to about 2.33:1, preferably in the range of 1.3:1 to 1.7:1, most preferably about 1.5:1. The preparation of the suspending agent is fully described the U.S. Pat. No. 5,366,742, above.

In the liquid suspensions the MCC:Alginate complex is suitably employed at a concentration in the range of 0.5 to 5 percent by weight of the suspension, preferably from about 0.7 to about 3 percent, but may vary with the pharmaceutical active ingredient being employed. For example for antacid suspensions the preferred range is from about 0.7 to about 1.5 weight percent, whereas for ibuprofen suspension the preferred range is from about 1 to about 3 weight percent. In the dry reconstitutible powder formulations the MCC:Alginate complex is suitably employed at a level in the range of about 0.5 to about 10% by weight of the dry formulation.

Xanthan gum, a commonly used additive in many pharmaceutical suspensions, may be advantageously used in the pharmaceutical suspension and reconstitutible dry powder formulations of this invention. Xanthan gum may suitably be employed in an amount sufficient to provide a concentration of about 0.05 to about 0.5 weight percent and, depending on the particular pharmaceutical active being suspended, preferably at a concentration in the range of about 0.08 to about 0.3 weight percent. In the case of antacid suspensions, the xanthan concentration is preferably in the range of about 0.08 to about 0.12 weight percent. For suspension of ibuprofen and acetaminophen, the preferred levels of xanthan gum are in the range of about 0.1 to about 0.3 weight percent.

It will be apparent to those skilled in the art that various other commonly used additives may be used in the suspensions and reconstitutible dry powders of this invention. For example, various sweetening, flavoring, and taste masking agents may be added to improve palatability of the suspensions, as well as pharmaceutically acceptable agents for adjusting the pH of the suspensions to a pH of at least 3.5, as more fully illustrated in example 2 below.

Various types of pharmaceutical actives may be formulated as suspensions, including antibiotics, analgesics and antipyretics, antihistamines, antacids, cough and cold preparations, anti-inflammatory agents, and bioadhesion or mucoadhesion agents. The following are specific examples of the various types of pharmaceuticals which may be employed in this invention: antibiotics such as erythromycin, cephalosporins, minocycline, and amoxicillin; analgesics, antipyretics, and anti-inflammatory agents such as acetaminophen, ibuprofen, ketoprofen, indomethacin, naproxen, acetaminophen with codeine, and acetaminophen with propoxyphene napsylate; antihistamines such as chlorpheniramine maleate, diphenhydramine hydrochloride, and triprolidine hydrochloride; antacids and gastrointestinal drugs such as calcium carbonate, aluminum hydroxide, magnesium hydroxide cimetidine, loperamide hydrochloride, ranitidine, and famotidine; and cough and cold preparations such as dextromethorphan hydrobromide, ephedrine sulfate, guiafenesin, phenylpropanolamine hydrochloride, promethazine hydrochloride, and pseudoephedrine hydrochloride.

The foregoing exemplary compounds, as well as other pharmaceutical actives which are not exemplified above, may be utilized in the suspensions of this invention, either alone or in combination with each other or with other pharmaceutical actives. At least one of the actives employed in these suspensions must be either insoluble or only slightly soluble in aqueous media. The invention is further exemplified in the working examples below with suspensions of acetaminophen, ibuprofen, or a metal hydroxide.

The level at which any pharmaceutical active ingredient is in suspension using the MCC:Alginate complex suspending agent will depend on several factors. One of the factors is the amount of active ingredient to be delivered in a standard amount of suspension, for example, 5 mL (1 teaspoon) or 15 mL (1 tablespoon). Another factor is the amount which can be suspended effectively. This latter factor is less limiting than the first factor, as is shown in Examples 5–7. For example, 1–20 percent of acetaminophen and 1–5 percent of ibuprofen, both on a dry weight basis, can be satisfactorily suspended with the suspending agent of the invention. In an antacid suspension based on the weight of the suspension, 20–30 weight percent of aluminum hydroxide gel and 10–20 weight percent of magnesium hydroxide paste can be successfully suspended using the suspending agent of the invention.

The following examples below illustrate the practice of the present invention. These examples are not intended to be limiting of the scope of the present invention but are to be read with the general and detailed description of the invention and the appended claims all of which provide a further understanding of the scope and content of the invention.

In the examples which follow, the terms indicated below have the meanings associated with them. AC-815 refers to attrited microcrystalline cellulose (85%) coprocessed with calcium/sodium alginate salt complex (15%), the preferred suspending agent of this invention. RC-591 refers to attrited microcrystalline cellulose (89%) coprocessed with carboxymethyl cellulose (11%), the suspending agent of above mentioned U.S. Pat. No. 4,427,681. CL-611 refers to attrited microcrystalline cellulose (85%) coprocessed with carboxymethylcellulose (15%), a product closely related to RC-591 but having the same weight ratio (85:15) of MCC to coprocessed additive as the preferred embodiment of this invention.

EXAMPLE 1

Comparison of Suspending Agents for Dispersibilty

In a 236.6 mL (8 oz.) bottle was placed 150 mL of deionized water. To this bottle was then added 3 grams of AC-815. After being capped, the bottle was shaken vigorously by hand for one minute. The suspension was then observed visually for the presence or absence of fish eyes, i.e., undispersed gelatinous-coated powder globules, and lumps of suspending agent. The suspension had a cloudy/watery appearance without any fish eyes or lumps. This observation was confirmed by examining a sample of the suspension under a light microscope. The other suspending agents were similarly evaluated for dispersibility. The results of these tests are shown in Table 1.

TABLE 1

| Suspending Agent | Appearance |
| --- | --- |
| AC-815 | No lumps present, suspension has a cloudy or watery appearance |
| RC-591 | Large undispersed lumps throughout suspension with thick cloudy appearance |
| CL-611 | Undispersed lumps appeared on top of suspension which was extremely cloudy and not well dispersed |
| Xanthan gum | Large undispersed lumps were suspended throughout a clear gel |
| SeaSpen ® PF[1] | Lumps floating on top of the suspension which has a creamy color |
| Sodium CMC[2] | A clear gel with undispersed lumps settling to the bottom |

[1]SeaSpen ® PF, carrageenan, calcium sulfate and trisodium orthophosphate (FMC Corporation, Philadelphia, PA 19103).
[2]Sodium carboxymethylcellulose, Aqualon ® 7MF (Aqualon Co., Wilmington, DE 19899).

The foregoing results illustrate the superiority of AC-815, the suspending agent of the invention, over numerous other known suspending agents. It produced the only true suspension and had no lumps or fish eyes.

EXAMPLE 2

Comparison of Stability of Suspending Agents at Various pH Levels and Upon Storage In a large beaker was placed 900 mL of deionized water to which was added 18 grams of AC-815. Dispersion of this mixture was achieved using a Scott Turbon mixer at 4640 rpm for 10 minutes. The dispersion was then divided into three 300 mL portions which were placed in 400 mL beakers. To the dispersion in one beaker was added 0.75 gram of citric acid to lower the pH. To a second portion was added three drops of sodium hydroxide solution to make the dispersion more basic. The two dispersions to which additions had been made were mixed as described above for 10 additional minutes. The pH of each dispersion was measured and recorded. Also, the viscosity of each dispersion was measured using a Brookfield DV-III viscometer fitted with spindle #2 operated at 12 rpm. The pH of each of these dispersions was 2.78, 5.38, and 9.00, and the viscosities were, respectively, 92.5 cps, 832 cps, and 880 cps. The results of this experiment and identical experiments with RC-591 and CL-611 are reported in Table 2 below.

TABLE 2

| AC-815 | | RC-591 | | CL-611 | |
| --- | --- | --- | --- | --- | --- |
| pH | Viscosity (cps) | pH | Viscosity (cps) | pH | Viscosity (cps) |
| 9.00 | 880 | 7.54 | 680 | 7.04 | 15 |
| 5.38 | 832 | 6.44 | 775 | 6.43 | 22.5 |
| 2.78 | 92.5 | 3.04 | 560 | 3.09 | 17.5 |

To test the stability of each of these dispersions, 75 mL of each dispersion was placed in four 118.3 mL (4 oz.) bottles, A bottle of each dispersion was stored for a period of one month at 4° C., room temperature 20° C., 35° C., and 45° C.

After two weeks the stability of the dispersions was visually assessed, and a second similar assessment of stability was made for each at the end of the month. The results recorded after one month of storage are shown in Table 3 below where + is a stable dispersion, − means slight separation, −− means increased separation, and −−− means severe separation.

TABLE 3

|  | Storage Temperature | | | |
| --- | --- | --- | --- | --- |
|  | 4° C. | 20° C. | 35° C. | 45° C. |
| AC-815 | | | | |
| pH = 9.00 | + | + | − | − |
| pH = 5.38 | + | + | + | + |
| pH = 2.78 | − | −− | −− | −−− |
| RC-591 | | | | |
| pH = 7.54 | +[a] | +[a] | +[a] | +[a] |
| pH = 6.44 | + | + | + | + |
| pH = 3.04 | + | + | + | + |
| CL-611 | | | | |
| pH = 7.04 | + | + | + | + |
| pH = 6.43 | + | + | + | + |
| pH = 3.09 | + | + | + | + |

[a]Although the dispersion was rated as being stable, air bubbles were present, indicating some form of instability.

This example illustrates that AC-815, the suspending agent of this invention, is quite stable at a pH in the range of about 3.5 to about 9, whereas RC-591 appeared foamy and gelatinous at a basic pH. The third suspending agent CL-611 produced viscosities which were too low to be useful.

EXAMPLE 3

Comparison of Viscosity Changes with Increased Mixing Times for Suspending Agents In a large beaker was placed 600 mL of deionized water. To this was added 12 grams of AC-815 and mixing was started with a Scott Turbon mixer operated at 4000 rpm. After 5 minutes and at 5 minute intervals thereafter, the mixer was stopped and the viscosity of the dispersion was measured using a Brookfield DV-III viscometer fitted with spindle #2 operated at 12 rpm. After 30 minutes of mixing, the final viscosity was determined. The identical procedure was followed using RC-591 and CL-611. The viscosities for these three suspending agents are summarized in Table 4 below.

TABLE 4

| 2 weight percent dispersions of each suspending agent | | | | | | |
| --- | --- | --- | --- | --- | --- | --- |
|  | Viscosity (cps) | | | | | |
| Mixing time (min) | 5 | 10 | 15 | 20 | 25 | 30 |
| AC-815 | 505 | 880 | 965 | 955 | 915 | 950 |
| RC-591 | 1380 | 872 | 680 | 525 | 432 | 420 |
| CL-611 | 85 | 42 | 22.5 | 25 | 26 | 17 |

An identical experiment was performed except that 18 grams of suspending agent was dispersed in 600 mL of deionized water. The results of this experiment are shown in Table 5 below.

TABLE 5

| 3 weight percent dispersions of each suspending agent | | | | | | |
| --- | --- | --- | --- | --- | --- | --- |
|  | Viscosity (cps) | | | | | |
| Mixing time (min) | 5 | 10 | 15 | 20 | 25 | 30 |
| AC-815 | 1330 | 2060 | 2359 | 2539 | 2609 | 2689 |
| RC-591 | 1172 | Gel formed - no viscosity measured. | | | | |
| CL-611 | 927 | 290 | 167 | 127 | 105 | 207 |

EXAMPLE 4

Comparison of Dispersibility of Suspending Agents

In a beaker 3 grams of AC-815 was dispersed in 300 mL of deionized water using a Scott Turbon mixer operated at 4700 rpm. The time required for the AC-815 to be fully dispersed was then measured. This experiment was repeated four times with different lots of this product. The average time required for complete dispersion was 26.25 seconds. This same experiment was repeated once each with RC-591 and CL-611. The former required 160 seconds for complete dispersion, and the latter required 90 seconds.

A second test of dispersibility of the same materials was done according to the following procedure. In a 354.9 mL (12 oz.) bottle was placed 300 mL of deionized water. To this bottle was added 3 grams of AC-815. The bottle was capped and shaken vigorously for one minute. This experiment was repeated four times with different lots of this product. In all cases the AC-815 dispersed easily without any lumps or subsequent separation. When the same experiment was tried using RC-591, there were many lumps of product undispersed which floated on top of the water. CL-611 behaved in a manner similar to AC-815.

These tests clearly demonstrate the superior dispersibility of AC-815 in reconstitutible pharmaceutical formulations.

EXAMPLE 5

Acetaminophen Reconstitutible Formulation Using AC-815 as the Suspending Agent

All components of this formulation were passed through a #16 U.S. Standard mesh screen before being used. In a twin shell blender (Patterson-Kelly) was placed 396 grams of sucrose. To the blender were added 2.3 grams potassium sorbate, 20.5 grams of sodium citrate dihydrate, 2.0 grams of anhydrous citric acid, and 130.4 grams of acetaminophen. The blender was operated for three minutes to mix this mixture thoroughly. At the conclusion of this period 396 grams of sucrose, 2.0 grams of xanthan gum and 50.8 grams of AC-815 were added to the blender which was operated for 8 minutes to complete the mixing. A portion of this formulation (88.66 grams) was placed in a 473.2 mL (16 oz.) wide-mouth Qorpac® jar. Then, 75 mL of deionized water was added to the contents of the jar, and the jar was capped and shaken vigorously for 30 seconds. A second portion of 75 mL of deionized water was added to the jar which, after being capped, was shaken for an additional 30 seconds. A portion (100 mL) of the suspension was poured into a 100 mL graduated cylinder fitted with a stopper. After standing for 30 minutes, the graduated cylinder was checked visually for separation of the suspension, but none was observed. Additional observations were made after 24 hours, one week, and two weeks. After 24 hours there was no separation, and after a week only 1% separation had occurred. After 2 weeks the separation had increased to 5%. The remaining portion of the dispersion was poured into a beaker, and the viscosity was measured using a Brookfield RVT viscometer equipped with a #3 spindle operated at 50 rpm. This formulation was prepared using four different lots of AC-815. The average viscosity of these formulations was 619 cps. For comparison, an identical formulation in which CL-611 replaced the AC-815 had a viscosity of 128 cps. This formulation had separation of 0.5% after 30 minutes, 5% separation after 24 hours, 15% separation after one week, and 30% separation after two weeks.

EXAMPLE 6

Ibuprofen Oral Suspension Using AC-815 as the Suspending Agent

In a large beaker stirred with a Lightnin® propeller mixer was placed 450 mL of deionized water. To the water was added 100 grams of sorbitol solution (70% sorbitol), USP, and the mixture was stirred until it was homogeneous. Next, 20 grams of AC-815 was added to the aqueous sorbitol solution which was mixed for about 5 minutes until the AC-815 was well dispersed and hydrated. Sucrose (350 grams) was added to the beaker and mixed until dissolved, Sodium benzoate NF (2.50 grams) and 0.05 gram of FD&C Red #40 dye were added to the mixture which was stirred until dissolution was complete. In a separate beaker 2 grams of xanthan gum was dispersed in 50 grams of glycerin. This dispersion was then added to the contents of the large beaker. In sequence, 2 grams of Polysorbate 80 and 20 grams of ibuprofen, USP, were added to the suspension which was stirred until it was uniform. Finally, 2.5 grams of orange flavor and 2 grams of citric acid were added, and the suspension was mixed until they were dissolved. The suspension was diluted to a volume of 2000 mL with of deionized water and mixed well until it was uniform. This suspension contained 100 mg of ibuprofen per 5 mL of suspension and had a specific gravity of 1.18 g/mL. The sedimentation of the suspension was determined by pouring 100 mL of the suspension into a 100 mL graduated cylinder fitted with a stopper. Visual observations of the sedimentation of the suspension stored at room temperature were made after 24 hours, one week, and one and two months. No sedimentation or separation was visible at any of these times. About 100 mL of the suspension was placed in a small beaker to obtain its viscosity. The viscosity measurement was made using a Brookfield RVT viscometer fitted with spindle #3 operated at 20 rpm. An initial viscosity measurement was made as well as one taken after the suspension had been sitting undisturbed for 24 hours. The viscosity both times was 2400 cps. Portions of the suspension were then placed in 473.2 mL (16 oz.) wide-mouth Qorpac® jars for storage at room temperature and 35° C. to determine the viscosity changes after storage for one and two months. The viscosity measurements were made as described above. After one month and two months storage at room temperature, the viscosity was 2300 cps. At 35° C., the viscosity dropped to 1800 cps after one month and dropped still further to 1400 cps after two months. Although this suspension decreased in viscosity at the elevated storage temperature, it appeared to be a physically stable and pharmaceutically elegant suspension.

EXAMPLE 7

Antacid Formulation Using AC-815 as the Suspending Agent

In a large beaker was placed 600 mL of deionized water. To the water was added 1.6 grams of methylparaben and 0.166 gram of propylparaben. This mixture was stirred with a Scott Turbon mixer at 1980 rpm until complete dissolution was achieved. Slowly the speed of the mixer was increased to 4000 rpm, and 14.4 grams of AC-815 was added slowly to the vortex of the stirred mixture. When the AC-815 was completely dispersed, 1.6 grams of xanthan gum was added slowly with continued mixing until the xanthan gum was completely dispersed. Next, 80 grams of sorbitol solution (70%) was added to the dispersion, and the container in which the sorbitol solution had been weighed was rinsed with 25 mL of deionized water which was added to the dispersion. The resulting mixture was mixed for five minutes at 4000 rpm. Magnesium hydroxide paste (207.04 grams) was added to the dispersion and was mixed for five minutes. Next, 391.36 grams of aluminum hydroxide gel was added to the dispersion and mixed for an additional five minutes at 4000 rpm. The container in which the aluminum hydroxide was weighed was rinsed with 50 mL of deionized water which was added to the dispersion. Deionized water (228.8 mL) was added and mixed for five minutes. The dispersion was then passed through a two-stage Gaulin homogenizer with the first stage operated at 17,236.9 kPa (2500 psi) and the second stage at 3,447.4 kPa (500 psi). A portion of this suspension was poured into a 236.6 mL (8 oz.) wide-mouth Qorpac® jar, and the initial viscosity was measured using a Brookfield RVT viscometer fitted with spindle #3 operated at 50 rpm. The initial viscosity was 480 cps. Two additional portions of this suspension were placed in 236.6 mL (8 oz.) wide-mouth Qorpac® jars. These three samples were stored at room temperature, 35° C., and 45° C. After four, eight, and twelve weeks the viscosity of each sample was again measured as described above. These viscosities are shown in Table 6 below. Also, the separation of this suspension was determined by measuring the thickness of the supernatant layer and the total height of the suspension in the jar. This was done for the three samples stored at room temperature and the elevated temperatures at the same time the viscosity was measured. These results are also shown in Table 6.

Table 6

| Storage Temperature °C. | 4 weeks | | 8 weeks | | 12 weeks | |
|---|---|---|---|---|---|---|
| | Viscosity cps | Separation % | Viscosity cps | Separation % | Viscosity cps | Separation % |
| 20 | 410 | 13.0 | 380 | 20.9 | 360 | 26.8 |
| 35 | 460 | 8.2 | 340 | 18.6 | 360 | 23.8 |
| 45 | 564 | 9.1 | 390 | 18.1 | 450 | 20.7 |

Although there was considerable separation during the extended storage time, when the suspension was shaken briefly by hand, it redispersed completely and easily.

What is claimed:

1. An improved pharmaceutical suspension consisting essentially of water, a pharmaceutically effective amount of a substantially water insoluble or slightly water soluble active ingredient, from 0.5% to 10% by weight of the suspension of suspending agent comprising 80% to 90% by weight attrited microcrystalline cellulose at least partially surface coated with 10% to 20% by weight of a calcium/sodium alginate salt complex barrier dispersant, said suspension having a pH of at least 3.5, and optionally sweetening, flavoring and taste masking agents.

2. The pharmaceutical suspension of claim 1 in which said suspending agent additionally comprises from 0.05% to 0.5% by weight xanthan gum.

3. The pharmaceutical suspension of claim 2 in which the active ingredient is selected from antibiotics, analgesics and antipyretics, antihistamines, antacids, cough and cold preparations, anti-inflammatory agents, and bioadhesion and mucoadhesion agents.

4. The pharmaceutical suspension of claim 3 in which the active ingredient comprises acetaminophen, ibuprofen or a metal hydroxide.

5. A hydratable, reconstitutible, dry powder pharmaceutical formulation comprising a pharmaceutically effective amount of a substantially water insoluble or slightly soluble active ingredient which is stable in aqueous media having a pH of at least 3.5 and a suspension stabilizing amount of suspending agent comprising 80% to 90% by weight attrited microcrystalline cellulose at least partially surface coated with 10% to 20% by weight of a calcium/sodium alginate salt complex barrier dispersant.

6. The pharmaceutical formulation of claim 5 in which said suspending agent additionally comprises from 0.05% to 0.5% by weight xanthan gum.

7. The pharmaceutical suspension of claim 6 in which the active ingredient is selected from antibiotics, analgesics and antipyretics, antihistamines, antacids, cough and cold preparations, anti-inflammatory agents, and bioadhesion and mucoadhesion agents.

8. The formulation of claim 7 in which the active ingredient is acetaminophen, ibuprofen or a metal hydroxide.

* * * * *